US00PP14290P29

(12) United States Plant Patent
Usrey

(10) Patent No.: US PP14,290 P2
(45) Date of Patent: Nov. 11, 2003

(54) MANDEVILLA PLANT NAMED 'MONREY'

(50) Latin Name: *Mandevilla X amabilis*
Varietal Denomination: Monrey

(75) Inventor: Bruce Usrey, Dayton, OR (US)

(73) Assignee: Monrovia Nursery Company, Azusa, CA (US)

( * ) Notice: Subject to any disclaimer, the term of this patent is extended or adjusted under 35 U.S.C. 154(b) by 0 days.

(21) Appl. No.: 10/162,987

(22) Filed: Jun. 5, 2002

(51) Int. Cl.[7] ..... A01H 5/00
(52) U.S. Cl. ..... Plt./232
(58) Field of Search ..... Plt./232

*Primary Examiner*—Kent Bell
*Assistant Examiner*—Louanne Krawczewicz Myers
(74) *Attorney, Agent, or Firm*—C. A. Whealy

(57) ABSTRACT

A distinct cultivar of Mandevilla plant named 'Monrey', characterized by its vining growth habit; glossy, dark green leaves; and large double pink-colored flowers with 20 petals per flower.

1 Drawing Sheet

Botanical classification/cultivar designation: *Mandevilla× amabilis* cultivar Monrey.

BACKGROUND OF THE INVENTION

The present Invention relates to a new and distinct cultivar of Mandevilla plant, botanically known as *Mandevilla× amabilis,* and hereinafter referred to by the name 'Monrey'.

The new Mandevilla is a naturally-occurring branch mutation of the *Mandevilla×amabilis* cultivar Monite, disclosed in U.S. Plant Pat. No. 12,123. The new Mandevilla was discovered and selected by the Inventor on Jun. 29, 2001 in a controlled environment in Azusa, Calif., within a population of plants of the cultivar Monite.

Asexual reproduction of the new cultivar by tissue culture in a laboratory in Azusa, Calif., since August, 2001, has shown that the unique features of this new Mandevilla are stable and reproduced true to type in successive generations.

SUMMARY OF THE INVENTION

Plants of the cultivar Monrey have not been observed under all possible environmental conditions. The phenotype may vary somewhat with variations in environment such as temperature and light intensity without, however, any variance in genotype.

The following traits have been repeatedly observed and are determined to be the unique characteristics of 'Monrey'. These characteristics in combination distinguish 'Monrey' as a new and distinct cultivar of Mandevilla:

1. Vining growth habit.
2. Glossy, dark green leaves.
3. Large double pink-colored flowers with 20 petals per flower.

Plants of the new Mandevilla differ from plants of the parent, the cultivar Monite, primarily in flower form as plants of the cultivar Monite have single flowers with five petals.

Plants of the new Mandevilla can be compared to plants of the double flower Mandevilla cultivar Rita Marie Green, disclosed in U.S. Plant Pat. No. 11,787. In side-by-side comparisons conducted in Azusa, Calif., plants of the new cultivar differed from plants of the cultivar Rita Marie Green in the following characteristics:

1. Plants of the new Mandevilla had about 20 petals per flower whereas plants of the cultivar Rita Marie Green had about 10 petals per flower.
2. Flower petals of plants of the new Mandevilla were not fused whereas flower petals of plants of the cultivar Rita Marie Green were fused.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new Mandevilla.

The photograph at the left of the sheet comprises a side perspective view of typical plants of 'Monrey' grown in a five-gallon container.

The photograph at the right of the sheet comprises a close-up view of typical flowers, flower buds and leaves of 'Monrey'.

DETAILED BOTANICAL DESCRIPTION

In the following description, color references are made to The Royal Horticultural Society Colour Chart, 1995 Edition, except where general terms of ordinary dictionary significance are used. Plants used for the above-mentioned photographs and description were about ten months old when the photographs and description were taken. Five-gallon containers with three plants each were grown under commercial production conditions in a clear polyethylene-covered greenhouse in Azusa, Calif. during the spring. During the production of the plants, day temperatures ranged from 27 to 32° C. and night temperatures ranged from 4 to 16° C.

Botanical classification: *Mandevilla×amabilis* cultivar Monrey.

Parentage: Naturally-occurring branch mutation of *Mandevilla×amabilis* cultivar Monite, disclosed in U.S. Plant Pat. No. 12,123.

Propagation:

*Type.*—By tissue culture.

*Time to initiate roots on a micro-propagated plant.*—About 30 days.

*Time to produce a rooted micro-propagated plant.*—About 200 days.

*Root description.*—Numerous, fibrous and freely branching.

Plant description:

*Form.*—Perennial evergreen flowering plant; twining vine. Plants initially upright, then vining and requiring support to maintain upright habit. Plants are typically pinched to enhance lateral branch development; potentially two lateral branches form at every node.

*Plant height* (*length*).—About 120 cm.

*Plant diameter, single plant.*—About 22 cm.

*Vigor.*—Vigorous.

*Lateral branches.*—Length: About 32 cm. Diameter: About 3 mm. Internode length: About 9 cm. Shape in cross-section: Round. Strength: Flexible, strong. Texture: Pubescent. Color: Young stems: 144A. Mature stems: 199A.

*Foliage description.*—Arrangement: Opposite, simple. Length: About 13 cm. Width: About 6.2 cm. Shape: Elliptic. Apex: Acuminate. Base: Cordate. Margin: Entire. Texture, upper and lower surfaces: Rugose, leathery, durable; upper surface, glabrous; lower surface, pubescence on veins. Luster: Upper surface, glossy; lower surface, dull. Venation pattern: Pinnate, arcuate. Petiole length: About 1.2 cm. Petiole diameter: About 5 mm. Color: Young foliage, upper and lower surfaces: 146A. Fully expanded foliage, upper surface: 147A. Fully expanded foliage, lower surface: 147B. Venation, upper surface: 145B. Venation, lower surface: 145C. Petiole: 144A to 144B.

Flower description:

*Flower type and habit.*—Large double flowers arranged in loose elongated racemes, racemes axillary. About 14 flowers and flower buds per raceme; at full flower, about two or three developing racemes per plant. Flowers face mostly outward and droop from their weight. Flowers persistent. Flowers not fragrant.

*Natural flowering season.*—Spring until frost in the autumn; flowering continuous.

*Flower longevity on the plant.*—About 10 to 14 days.

*Inflorescence length.*—About 28 cm.

*Inflorescence width.*—About 12.5 cm.

*Flowers.*—Appearance: Double flower form; flowers rounded. Diameter: About 11 cm. Depth (length): About 6 cm.

*Flower buds* (*just showing color*).—Length: About 2.4 cm. Diameter: About 1 cm. Shape: Ovoid. Color: 155A; towards apex, 155A tinged with 56A.

*Petals.*—Quantity per flower: About 20 arranged in multiple whorls; overlapping; petals not fused at base. Length: About 6.5 cm. Width: About 6 cm. Shape: Obovate to roughly spatulate. Apex: Rounded, occasionally emarginate. Base: Obtuse. Margin: Entire, sinuate; undulate. Texture, upper and lower surfaces: Smooth, velvety, slightly ruffled. Color: When opening, upper surface: 62B. When opening, lower surface: 62C to 62D; towards base, 155A. Fully opened, upper surface: Towards margin, 62A; center, 62B; towards base, 62C; at base; 17A. Color becomes closer to 62C to 62D with subsequent development. Fully opened, lower surface: 62D; towards base, 155A.

*Sepals.*—Quantity: Five per flower in a single whorl; star-shaped calyx. Length: About 8 mm. Width: About 3 mm. Shape: Triangular. Apex: Acuminate. Base: Truncate. Margin: Entire. Texture, upper and lower surfaces: Smooth, glabrous. Color, upper and lower surfaces: 144A; towards apex, tinged with 60B.

*Peduncles.*—Length: About 18 cm. Diameter: About 3 mm. Angle: About 30° from stem. Strength: Flexible, moderately strong. Color: 144A.

*Pedicles.*—Length: About 5 cm. Diameter: About 2.5 mm. Angle: About 30 to 40° from stem. Strength: Flexible, moderately strong. Color: 144A.

*Reproductive organs.*—Stamens: Quantity per flower: No true stamens, about five to seven sterile staminodes. Anther shape: Spatulate, elongated. Anther length: About 7 mm. Anther color: 16C. Pollen: None observed. Pistils: None observed.

*Seed/fruit.*—Seed and fruit production has not been observed.

Disease/pest resistance: Plants of the new Mandevilla have not been noted to be resistant to pathogens and pests common to Mandevilla.

Weather tolerance: Plants of the new mandevilla have been observed to be tolerant to rain and wind and tolerant to temperatures from 0 to 43° C.

It is claimed:

1. A new and distinct cultivar of Mandevilla plant named 'Monrey', as illustrated and described.

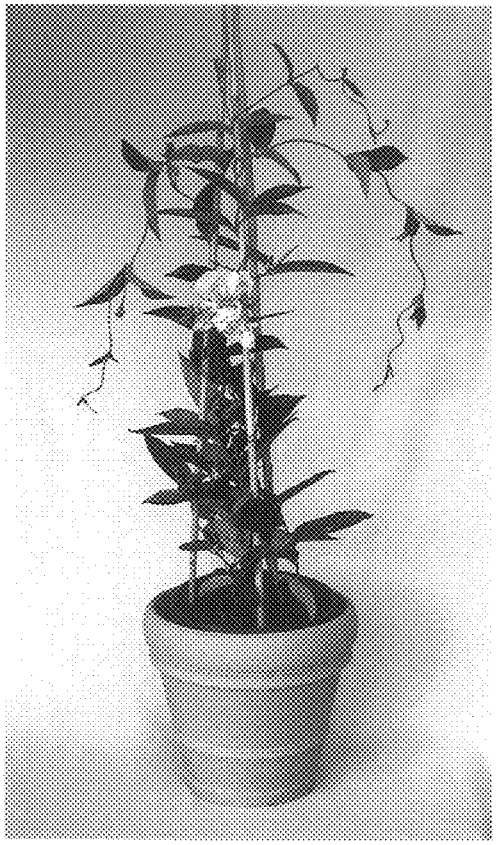
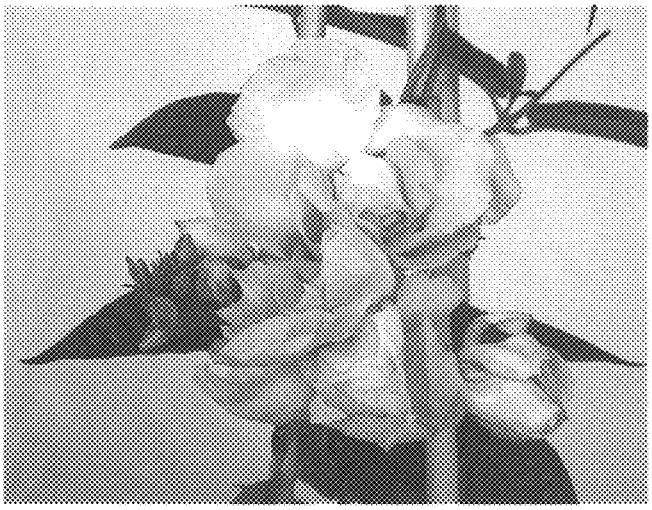

* * * * *